United States Patent
Diwu et al.

(10) Patent No.: US 10,239,853 B1
(45) Date of Patent: Mar. 26, 2019

(54) POLYCYCLIC PHOSPHORAMIDTES AND THEIR APPLICATIONS

(71) Applicant: AAT BIOQUEST, INC., Sunnyvale, CA (US)

(72) Inventors: Zhenjun Diwu, Sunnyvale, CA (US); Ruogu Peng, San Jose, CA (US); Haitao Guo, Santa Clara, CA (US); Zhen Luo, San Mateo, CA (US)

(73) Assignee: AAT Bioquest, Inc., Sunnyvale, CA (US)

( * ) Notice: Subject to any disclaimer, the term of this patent is extended or adjusted under 35 U.S.C. 154(b) by 0 days.

(21) Appl. No.: 15/998,019

(22) Filed: Jun. 12, 2018

(51) Int. Cl.
*C07D 307/77* (2006.01)
*G01N 33/58* (2006.01)

(52) U.S. Cl.
CPC ......... *C07D 307/77* (2013.01); *G01N 33/582* (2013.01)

(58) Field of Classification Search
CPC .............................. C07D 307/77; G01N 33/582
See application file for complete search history.

(56) References Cited

U.S. PATENT DOCUMENTS 5,583,236 A   12/1996   Brush

OTHER PUBLICATIONS

Ota et al., 26(3) Nucleic Acid Research 735-743 (1998) (CAS Abstract) (Year: 1998).*
Urdea, et al., "A comparison of non-radiosotopic hybridization assay methods using fluorescent . . . ," Nucleic Acids Research (1988) vol. 16(11): pp. 4937-4956.
Haralambidis, et al., "The Solid Phase Synthesis of Oligonucleotides containing a 3'-Peptide . . . ," Pergamon Journals Ltd. (1987) vol. 28(43) pp. 5199-5202.

* cited by examiner

*Primary Examiner* — Timothy R Rozof
(74) *Attorney, Agent, or Firm* — Jeffrey A. McKinney; McKinney Law Group APC

(57) ABSTRACT

The present invention is generally directed to fluorescent dyes useful for preparing fluorescent oligonucleotides, and the use of the fluorescent oligonucleotides for the detection, discrimination and quantification of molecular biology targets.

20 Claims, 4 Drawing Sheets

Specification includes a Sequence Listing.

US 10,239,853 B1

POLYCYCLIC PHOSPHORAMIDTES AND THEIR APPLICATIONS

REFERENCE TO SEQUENCE LISTING SUBMITTED VIA EFS-WEB

This application includes an electronically submitted sequence listing in .txt format. The .txt file contains a sequence listing entitled "AA-006.02 ST25.txt" created on Jul. 24, 2018 and is 642 bytes in size. The sequence listing contained in this .txt file is part of the specification and is hereby incorporated by reference herein in its entirety.

BACKGROUND

Fluorescent labeling, one of the most dominant non-radioactive biological detection modalities, is a highly desirable method for the detection of nucleic acids. For example, this method is useful in automated DNA sequencing, in situ detection of hybridization, detection of PCR products, structural studies, and any of several other applications (G. C. Howard, Methods in Nonradioactive Detection, 1993; L. J. Kricka, Nonisotopic Probing, Blotting and Sequencing, 1995). In the past, the labelling of oligonucleotides has been most conveniently accomplished on an automated synthesizer by introduction of a derivatized deoxyuridine phosphoramidite or a linker phosphoramidite bearing a protected primary amine or thiol group. Consequently, the preparation of a labelled oligonucleotide requires synthesis of an oligonucleotide bearing the aforementioned modifications. The oligomer is deprotected, liberating the nucleophile, which can react with a fluorescent label or other tags. This procedure entails at least a partial purification of the deprotected oligomer, reaction with the fluorescent dye derivative (such as a fluorescent dye succinimidyl ester, isothiocynate, sulfonyl chloride or maleimide, etc.), removal of the excess reagent, and purification of the labelled oligomer. The addition of the label (e.g., a fluorescent dye) by an extra step, and the additional step for purifying the labeled product are often tedious, which increases synthesis time considerably (S. Ochet, et al., Tetrahedron 1988, 43, 3481; J. Haralambidis, et al., Tetrahedron Lett. 1987, 28, 5199; M. S., Urdea et al., Nucl. Acids Res. 1988, 16, 4937; S. Le Brun, et al., J. Biochemie 1989, 71, 319). The overall process requires approximately two days, compared to a few hours for preparation of the corresponding unlabeled oligonucleotides. In contrast, fluorescent dye phosphramidites enable the rapid preparation of fluorescent oligonucleotides just as the unlabeled oligonucleotides.

Fluoresceins have long been known for their fluorescent properties and are quite useful in labelling biomolecules. They have a very high absorbance with excellent fluorescence quantum yields, considering to be among the most popular fluorescent dyes used in labelling oligonucleotides. One prior art method described a method to link a fluorescein to oligonucleotides through fluorescein phosphoramidite chemistry (U.S. Pat. No. 5,583,236). However, all the oligonucleotides prepared from the known fluorescein phosphoramidites have significantly reduced fluorescence at physiological pH (~7.0) due to the high pKa of fluoresceins used for preparing fluorescein phosphoramidites. Another drawback for the existing fluorescein-labeled oligonucleotides results from the low photostability of the fluoresceins used for preparing fluorescein phosphoramidites, which limits the assay performance with the fluorescein-labeled oligonucleotides. The third drawback for the existing fluorescein-labeled oligonucleotides is that their short excitation and emission wavelengths severely overlap with the wavelengths of many natural substances in cells or biological samples, resulting in high assay background.

The compound of this invention eliminates the above described drawbacks of the existing fluorescein phosphoramidites. The oligonucleotides prepared from these new fluorescein derivatives have red-shifted wavelengths, reduced pKa and enhanced photostability. Under the same conditions, the fluorescence detections performed with the oligonucleotides prepared from the new fluorescein derivatives of this invention demonstrate low assay background, high sensitivity and enhanced photostability.

DEFINITIONS

Figure 1:
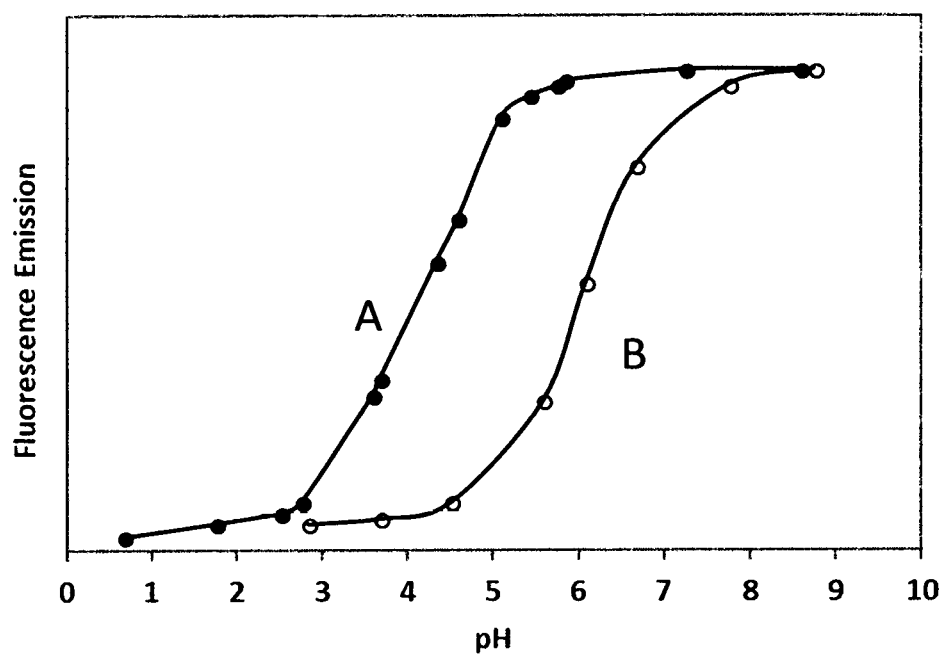
FIG. 1. The fluorescence intensity comparison of fluorescent dye-labeled oligonucleotides at different pHs. The fluorescent dye-labeled oligonucleotides are in the form of [dye]-CGACGGAGTCCTTCCACGATACCACGTCG (SEQ ID NO: 1). A: The dye-labeled oligonucleotide prepared from Compound 20; B: The dye-labeled oligonucleotide prepared from 6-FAM phosphoramidite, AAT Bioquest;). As seen from FIG. 1, Oligonucleotide A has the maximum fluorescence intensity in the entire pH range from 6 to 8 (the most common pH range used in biological assays) while Oligonucleotide B has its fluorescence intensity that is greatly changed from pH 6 to 8.
Figure 2:
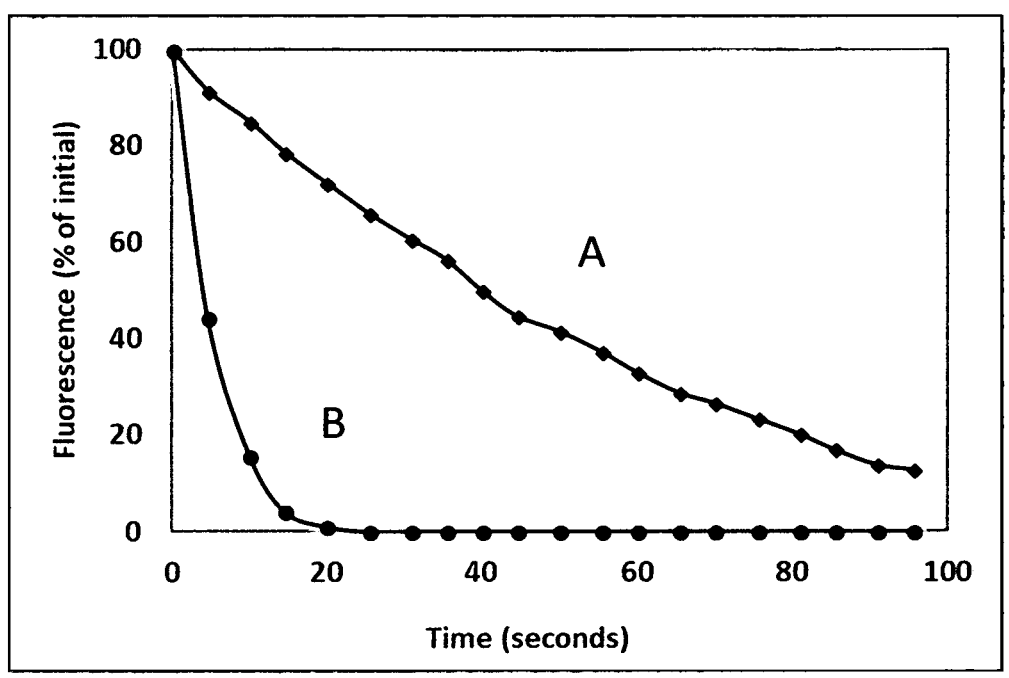
FIG. 2. The photostability comparison of fluorescent dye-labeled oligonucleotides. The fluorescent dye-labeled oligonucleotides are in the form of [dye]-CGACGGAGTCCTTCCACGATACCACGTCG (SEQ ID NO: 1). The oligonucleotides prepared from Compound 20 (A) and 6-FAM phosphoramidite (B) are illuminated under the same conditions. As seen from FIG. 2, Oligonucleotide A is much more resistant to photobleaching than Oligonucleotide B.
Figure 3:
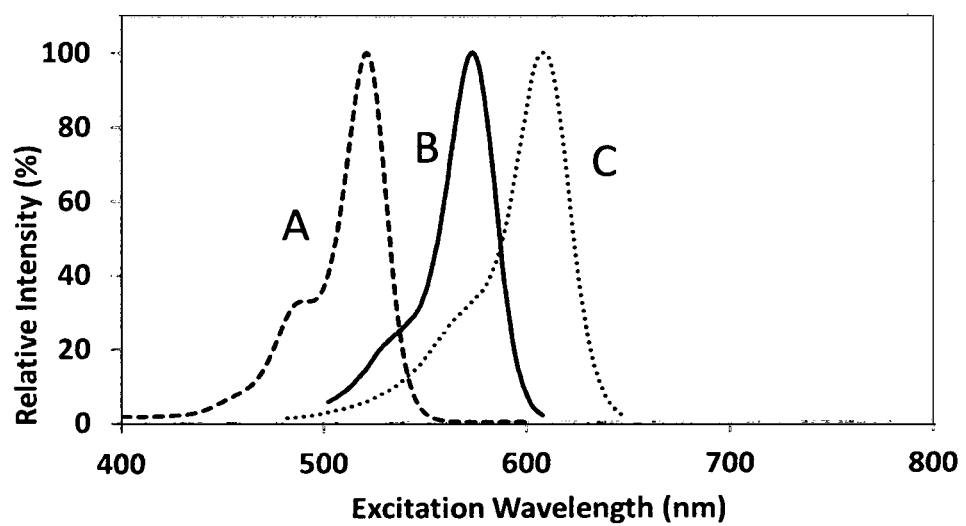
FIG. 3. The excitation wavelength comparison of fluorescent dye-labeled oligonucleotides at pH=7.0. The fluorescent dye-labeled oligonucleotides are in the form of [dye]-CGACGGAGTCCTTCCACGATACCACGTCG (SEQ ID NO: 1). As seen from FIG. 3, the oligonucleotide (B) prepared from carbofluorescein phosphoramidite (Compound 35) and the oligonucleotide (C) prepared from silyl fluorescein phosphoramidite (Compound 48) have much longer excitation wavelengths than the excitation wavelength of the oligonucleotide (A) prepared from the corresponding conventional fluorescein phosphoramidite (Compound 50).
Figure 4:
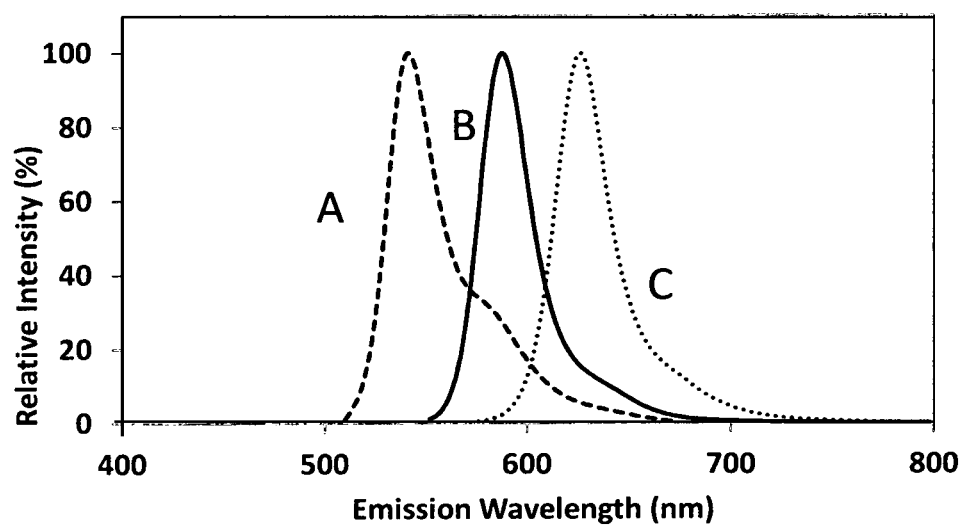
FIG. 4. The fluorescence wavelength comparison of fluorescent dye-labeled oligonucleotides at pH=7.0. The fluorescent dye-labeled oligonucleotides are in the form of [dye]-CGACGGAGTCCTTCCACGATACCACGTCG (SEQ ID NO: 1). As seen from FIG. 3, the oligonucleotide (B) prepared from carbofluorescein phosphoramidite (Compound 35) and the one (C) prepared from silyl fluorescein phosphoramidite (Compound 48) have much longer fluorescence wavelengths than the fluorescence wavelength of the oligonucleotide (A) prepared from the corresponding conventional fluorescein phosphoramidite (Compound 50).

The following definitions are set forth to illustrate and define the meaning and scope of the various terms used to describe the invention herein.

The term "phosphoramidite" as used herein, refers to a monoamide of a phosphite diester with a typical formula "$(R_1O)(R_2O)-P-NR_3R_4$". The key feature of phosphoramidites is their markedly high reactivity towards nucleophiles catalyzed by 1H-tetrazole or its equivalents. In these reactions, the incoming nucleophile replaces the $NR_3R_4$ moiety.

The term "oligonucleotide" as used herein, refers to an oligomer of DNA, RNA, or modifications thereof, in the range of 3 to 200 bases in length.

The term "organic substituent", as used herein, refers to a carbon-containing organic radical that incorporates straight, branched chain or cyclic radicals having up to 50 carbons, unless the chain length or ring size is limited thereto. The organic substituent may include one or more elements of unsaturation, such as carbon-carbon double or triple bonds. Organic substituents may include alkyl, alkylene, alkenyl, alkenylene and alkynyl moieties, among others.

The term "alkyl," as used herein, by itself or as part of another group, refers to straight, branched chain or cyclic radicals having up to 50 carbons, unless the chain length or ring size is limited thereto, such as methyl, ethyl, propyl, cyclopropanyl, isopropyl, butyl, t-butyl, isobutyl, pentyl, hexyl, cyclohexyl, isohexyl, heptyl, 4,4-dimethylpentyl, octyl, 2,2,4-trimethylpentyl, nonyl, and decyl, among others.

The term "alkylene," as employed herein, by itself or as part of another group, refers to straight, branched chain or cyclic divalent radicals having up to 50 carbons, unless the chain length or ring size is limited thereto. Typical examples include methylene (—$CH_2$—), ethylene (—$CH_2CH_2$—), propylene, butylene, pentylene, hexylene, heptylene, octylene, nonylene, and decylene, among others.

The term "alkenyl," as used herein, by itself or as part of another group, means a straight, branched chain or cyclic radical having 2-50 carbon atoms and one or more carbon-carbon double bonds, unless the chain length or ring size is limited thereto, such as ethenyl, 1-propenyl, 2-propenyl, 2-methyl-1-propenyl, 1-butenyl, and 2-butenyl, among others. The alkenyl chain may be 2 to 10 carbon atoms in length. Alternatively, the alkenyl chain may be 2 to 4 carbon atoms in length.

The term "alkenylene," as used herein, by itself or as part of another group, means straight, branched chain or cyclic divalent radical having 2-50 carbon atoms, unless the chain length or ring size is limited thereto, said straight, branched chain or cyclic radical containing at least one carbon-carbon double bond. Typical examples include ethenylene (—CH=CH—), propenylene (—CH=$CHCH_2$— and —$CH_2$CH=CH—), n-butenylene, and 3-methyl-2-pentenylene, hexenylene, heptenylene, octenylene, nonenylene, and decenylene, among others.

The term "alkynyl," as used herein, by itself or as part of another group, means a straight, branched chain or cyclic radical of 2-50 carbon atoms, unless the chain length or ring size is limited thereto, having at least one carbon-carbon triple bond between two of the carbon atoms in the chain, such as acetylenyl, 1-propynyl, and 2-propynyl, among others. The alkynyl chain may be 2 to 10 carbon atoms in length. Alternatively, the alkynyl chain may be from 2 to 4 carbon atoms in length.

The term "alkynylene" as used herein, by itself or as part of another group, means a straight, branched chain or cyclic divalent radical having 2-50 carbon atoms, unless the chain or length or ring size is limited thereto, that contains at least one carbon-carbon triple bond. Typical examples include ethynylene (—C≡C—), propynylene (—C≡$CCH_2$— and —$CH_2$C≡C—), n-butynylene, 4-methyl-2-pentynylene, 1-butynylene, 2-butynylene, 3-butynylene, 4-butynylene, pentynylene, hexynylene, heptynylene, octynylene, nonynylene, and decynylene, among others.

The term "alkoxy" as used herein, by itself or as part of another group, refers to any of the above radicals linked via an oxygen atom. Typical examples include methoxy, ethoxy, isopropyloxy, sec-butyloxy, n-butyloxy, t-butyloxy, n-pentyloxy, 2-methylbutyloxy, 3-methylbutyloxy, n-hexyloxy, and 2-ethylbutyloxy, among others. Alkoxy also may include PEG groups (—$OCH_2CH_2O$—) or alkyl moieties that contain more than one oxygen atom.

The term "aryl," as employed herein, by itself or as part of another group, refers to an aryl or aromatic ring system containing 1 to 4 unsaturated rings (each ring containing 6 conjugated carbon atoms and no heteroatoms) that are optionally fused to each other or bonded to each other by carbon-carbon single bonds, that is optionally further substituted as described below. Examples of aryl ring systems include, but are not limited to, substituted or unsubstituted derivatives of phenyl, biphenyl, o-, m-, or p-terphenyl, 1-naphthyl, 2-naphthyl, 1-, 2-, or 9-anthryl, 1-, 2-, 3-, 4-, or 9-phenanthrenyl and 1-, 2- or 4-pyrenyl. Aryl substituents may include phenyl, substituted phenyl, naphthyl or substituted naphthyl.

The term "heteroaryl," as employed herein, by itself or as part of another group, refers to groups having 5 to 14 ring atoms; 6, 10 or 14 π electrons shared in a cyclic array; and containing carbon atoms and 1, 2, 3, or 4 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, carbazolyl, phenanthridinyl, acridinyl, perimidinyl, phenanthrolinyl, phenazinyl, isothiazolyl, phenothiazinyl, isoxazolyl, furazanyl, phenoxazinyl, and tetrazolyl groups).

Any aryl or heteroaryl ring system is unsubstituted or optionally and independently substituted by any synthetically accessible and chemically stable combination of substituents, such as H, halogen, cyano, sulfo, alkali or ammonium salt of sulfo, nitro, carboxy, alkyl, perfluoroalkyl, alkoxy, alkylthio, amino, monoalkylamino, dialkylamino or alkylamido, the alkyl portions of which having 18 or fewer carbons.

The terms "halogen" or "halo" as employed herein, by itself or as part of another group, refers to chlorine, bromine, fluorine or iodine.

The terms "amino" or "amine" include $NH_2$, "monoalkylamine" or "monoalkylamino," and "dialkylamine" or "dialkylamino". The terms "monoalkylamine" and "monoalkylamino," "dialkylamine" and "dialkylamino as employed herein, by itself or as part of another group, refers to the group $NH_2$ where one hydrogen has been replaced by an alkyl group, as defined above.

The terms "dialkylamine" and "dialkylamino" as employed herein, by itself or as part of another group, refers to the group $NH_2$ where both hydrogens have been replaced by alkyl groups, as defined above.

The term "hydroxyalkyl," as employed herein, by itself or as part of another group, refers to an alkyl group where one or more hydrogens thereof are substituted by one or more hydroxyl moieties.

The term "haloalkyl," as employed herein, by itself or as part of another group, refers to an alkyl group where one or more hydrogens thereof are substituted by one or more halo moieties. Typical examples include chloromethyl, fluoromethyl, difluoromethyl, trifluoromethyl, trichloroethyl, trifluoroethyl, fluoropropyl, and bromobutyl, among others.

The term "haloalkenyl," as employed herein, by itself or as part of another group, refers to an alkenyl group where one or more hydrogens thereof are substituted by one or more halo moieties.

The term "haloalkynyl," as employed herein, by itself or as part of another group, refers to an alkynyl group where one or more hydrogens thereof are substituted by one or more halo moieties.

The term "carboxyalkyl," as employed herein, by itself or as part of another group, refers to an alkyl group where one or more hydrogens thereof are substituted by one or more carboxylic acid moieties.

The term "heteroatom" as used herein, by itself or as part of another group, means an oxygen atom ("O"), a sulfur atom ("S") or a nitrogen atom ("N"). It will be recognized that when the heteroatom is nitrogen, it may form an $NR_1R_2$ moiety, where $R_1$ and $R_2$ are, independently from one another, hydrogen or alkyl, or together with the nitrogen to which they are bound, form a saturated or unsaturated 5-, 6-, or 7-membered ring.

DESCRIPTION OF THE PREFERRED EMBODIMENTS

The present application is directed to dye phosphoramidites useful for preparing fluorescent oligonucleotides used for the detection, discrimination and quantification of biological targets and events.

In one aspect of the invention, the compounds of the invention may be described by Formula 1:

Formula 1

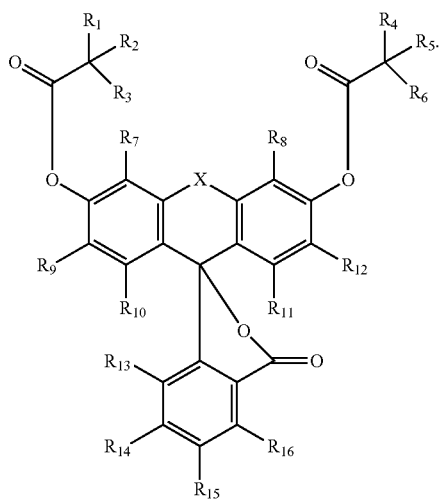

In certain cases, the substituents of Formula 1 are defined as in compounds 1.1-1.12 below.

1.1. In this embodiment, $R_1$-$R_6$ are independently a hydrogen, an alkyl, an aryl or a heteroaryl; $R_7$-$R_{16}$ are independently H, an alkyl, a halogen, carboxy, an alkoxy, an aryloxy, thiol, a alkylthiol, an arylthiol, azido, nitro, nitroso, cyano, an amino, hydroxy, a phosphonyl, a sulfonyl, a carbonyl, a boronyl, an aryl, a heteroaryl, or a phosphoramidite; X is N—$R_{18}$, P—$R_{18}$, O=P—$R_{18}$, O=P—$OR_{18}$, $R_{18}$—C—$R_{19}$, $R_{18}$—Si—$R_{19}$, S, O=S—$R_{18}$ or O=S(O)—$R_{18}$; provided that one of $R_7$-$R_{19}$ is L-O—P(O—$R_{20}$)($NR_{21}R_{22}$) wherein L is none or a linker, $R_{18}$ to $R_{22}$ are an alkyl, an aryl or a heteroaryl.

1.2. In one aspect of the invention, $R_1$-$R_6$ are independently a hydrogen or an alkyl; $R_7$-$R_{16}$ are independently H, an alkyl, a halogen, an aryl, a heteroaryl, or a phosphoramidite; X is N—$R_{18}$, P—$R_{18}$, O=P—$R_{18}$, O=P—$OR_{18}$, $R_{18}$—C—$R_{19}$, S, O=S—$R_{18}$ or O=S(O)—$R_{18}$; provided that one of $R_7$-$R_{19}$ is L-O—P(O—$R_{20}$)($NR_{21}R_{22}$) wherein L is none or a linker, $R_{18}$ to $R_{22}$ are an alkyl, an aryl or a heteroaryl.

1.3. In another aspect of the invention, $R_1$-$R_6$ are methyl; $R_7$-$R_{16}$ are independently H, chloro or fluoro, an aryl, a heteroaryl, or a phosphoramidite; X is O=P—$R_{18}$, O=P—$OR_{18}$, $R_{18}$—C—$R_{19}$, $R_{18}$—Si—$R_{19}$; provided that one of $R_7$-$R_{19}$ is L-O—P(O—$R_{20}$)($NR_{21}R_{22}$) wherein L is none or a linker, $R_{18}$ to $R_{22}$ are an alkyl.

1.4. In another aspect of the invention, $R_1$-$R_6$ are methyl; $R_7$-$R_{16}$ are independently H, chloro, fluoro, an aryl, a heteroaryl, or phosphoramidite; X is $R_{18}$—C—$R_{19}$ or $R_{18}$—Si—$R_{19}$; provided that one of $R_7$-$R_{19}$ is L-O—P(O—$CH_2CH_2CN$)($NR_{21}R_{22}$) wherein L is an alkyl linker, and $R_{21}$ and $R_{22}$ are isopropyl.

1.5. In another aspect of the invention, $R_1$-$R_6$ are methyl; $R_7$-$R_{16}$ are independently H, chloro, fluoro, an aryl, a heteroaryl, or phosphoramidite; X is $R_{18}$—C—$R_{19}$ or $R_{18}$—Si—$R_{19}$ wherein Rig and $R_{19}$ combine to form a 3-8 member ring structure; provided that one of $R_7$-$R_{19}$ is L-O—P(O—$CH_2CH_2CN$)($NR_{21}R_{22}$) wherein L is an alkyl linker, and $R_{21}$ and $R_{22}$ are isopropyl.

1.6. In another aspect of the invention, $R_1$-$R_6$ are methyl; $R_7$-$R_{16}$ are independently H, chloro, fluoro, an aryl, a heteroaryl, or phosphoramidite; X is $R_{18}$—C—$R_{19}$ or $R_{18}$—Si—$R_{19}$ wherein $R_{18}$ and $R_{19}$ combine to form cyclohexyl; provided that one of $R_7$-$R_{19}$ is L-O—P(O—$CH_2CH_2CN$)($NR_{21}R_{22}$) wherein L is an alkyl linker, and $R_{21}$ and $R_{22}$ are isopropyl.

1.7. In another aspect of the invention, $R_1$-$R_6$ are independently a hydrogen or an alkyl wherein $R_2$ and $R_3$ or $R_5$ and $R_6$ combine to form a 3-8 membered ring structure; $R_7$-$R_{16}$ are hydrogen, chloro, fluoro or a phosphoramidite; X is $R_{18}$—C—$R_{19}$ or $R_{18}$—Si—$R_{19}$; provided that one of $R_7$-$R_{19}$ is L-O—P(O—$CH_2CH_2CN$)($NR_{21}R_{22}$) wherein L is an alkyl linker, and $R_{21}$ and $R_{22}$ are isopropyl.

1.8. In another aspect of the invention, $R_1$ and $R_4$ are hydrogen; $R_2$ and $R_3$ combine to form cyclohexyl; $R_5$ and $R_6$ combine to form cyclohexyl; $R_7$-$R_{16}$ are hydrogen, chloro, fluoro or a phosphoramidite; X is $CH_3$—C—$CH_3$ or $CH_3$—Si—$CH_3$; provided that one of $R_7$-$R_{19}$ is L-O—P(O—$CH_2CH_2CN$)($NR_{21}R_{22}$) wherein L is an alkyl linker, and $R_{21}$ and $R_{22}$ are isopropyl.

1.9. In another aspect of the invention, $R_1$-$R_6$ are methyl; $R_7$-$R_{13}$, $R_{15}$ and $R_{16}$ are independently H, chloro or fluoro; $R_{14}$ is C(=O)NH($CH_2$)$_n$—O—P(O—$CH_2CH_2CN$)($NR_{21}R_{22}$) wherein n is 2-20, and $R_{21}$ and $R_{22}$ are isopropyl.

1.10. In another aspect of the invention, $R_1$-$R_6$ are methyl; $R_7$-$R_{14}$ and $R_{16}$ are independently H, chloro or fluoro; $R_{15}$ is C(=O)NH($CH_2$)$_n$—O—P(O—$CH_2CH_2CN$)($NR_{21}R_{22}$) wherein n is 2-20, and $R_{21}$ and $R_{22}$ are isopropyl.

1.11. In another aspect of the invention, $R_1$-$R_6$ are methyl; $R_7$-$R_{14}$ and $R_{16}$ are independently H, chloro or fluoro; $R_{15}$ is C(=O)NH($CH_2CH_2O$)$_n$—O—P(O—$CH_2CH_2CN$)($NR_{21}R_{22}$) wherein n is 2-20, and $R_{21}$ and $R_{22}$ are isopropyl.

1.12. In another aspect of the invention, $R_1$-$R_6$ are methyl; $R_7$-$R_{13}$, $R_{15}$ and $R_{16}$ are independently H, chloro or fluoro; $R_{14}$ is C(=O)NH($CH_2CH_2O$)$_n$—O—P(O—$CH_2CH_2CN$)($NR_{21}R_{22}$) wherein n is 2-20, and $R_{21}$ and $R_{22}$ are isopropyl.

The oligonucleotides prepared from compounds 1.1, 1.2, 1.3, 1.4, 1.5, 1.6, 1.7, 1.8, 1.9, 1.10, 1.11 and 1.12 typically have much longer wavelengths than the excitation wavelength of oligonucleotides prepared from Formula 2. Oftentimes, the excitation wavelength of the oligonucleotides prepared from compounds of the invention is above 550 nm. In certain cases, the oligonucleotides prepared from the compounds of the invention exhibit excitation wavelengths above about 575 nm or 600 nm.

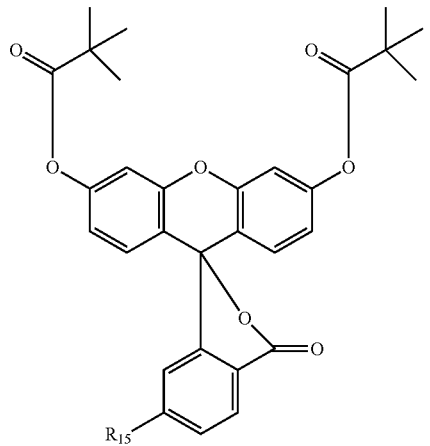

Formula 2

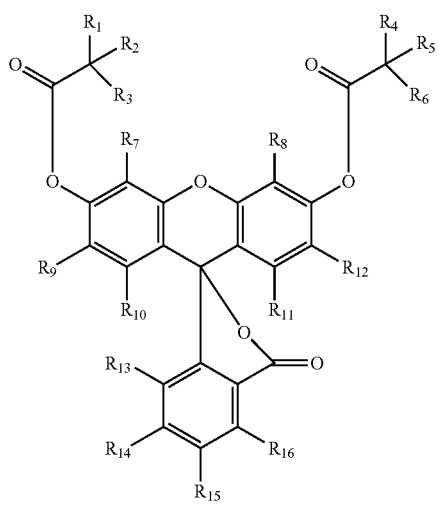

Formula 3

The oligonucleotides prepared from compounds 1.1, 1.2, 1.3, 1.4, 1.5, 1.6, 1.7, 1.8, 1.9, 1.10, 1.11 and 1.12 typically have much longer fluorescence wavelengths than the fluorescence wavelength of oligonucleotides prepared from Formula 2, where $R_{15}$ is $C(=O)NH(CH_2)_6—O—P(O—CH_2CH_2CN)(N\text{-}iPr_2)$. In certain cases, the compounds exhibit fluorescence wavelengths above about 575 nm or 600 nm.

Oligonucleotides prepared from and/or including the compounds 1.1, 1.2, 1.3, 1.4, 1.5, 1.6, 1.7, 1.8, 1.9, 1.10, 1.11 and 1.12 typically are substantially more resistant to photobleaching than oligonucleotides prepared from and/or including the compound of Formula 2. Oftentimes the oligonucleotides exhibit at least twice the percentage of initial fluorescence after 30 seconds when illuminated under the same conditions. In certain cases, the oligonucleotides exhibit at least three times, four times, five times, six times, seven times, eight times, nine times or ten times the percentage of initial fluorescence.

Oligonucleotides prepared from and/or including the compounds 1.1, 1.2, 1.3, 1.4, 1.5, 1.6, 1.7, 1.8, 1.9, 1.10, 1.11 and 1.12 typically have much longer wavelengths than the excitation wavelength of oligonucleotides prepared from and/or including a compound of Formula 2. Oftentimes, the excitation wavelength of the oligonucleotides is above 550 nm. In certain cases, the oligonucleotides exhibit excitation wavelengths above about 575 nm or 600 nm.

Oligonucleotides prepared from and/or including the compounds 1.1, 1.2, 1.3, 1.4, 1.5, 1.6, 1.7, 1.8, 1.9, 1.10, 1.11 and 1.12 typically have much longer fluorescence wavelengths than the fluorescence wavelength of oligonucleotides prepared from and/or including a compound of Formula 2. In certain cases, the oligonucleotides exhibit fluorescence wavelengths above about 575 nm or 600 nm.

In another aspect of the invention, the compounds of the invention may be described by Formula 3:

In certain cases, the substituents of Formula 3 are defined as in compounds 3.1-3.8 below.

3.1. In this embodiment, $R_1$-$R_6$ are independently a hydrogen or an alkyl; $R_7$-$R_{16}$ are hydrogen, chloro, fluoro or a phosphoramidite; provided that at least two of $R_7$-$R_{16}$ are fluoro, and one of $R_7$-$R_{16}$ is L-O—P(O—$R_{20}$)(N$R_{21}R_{22}$) wherein L is none or a linker, and $R_{20}$ to $R_{22}$ are an alkyl or an aryl.

3.2. In another aspect of the invention, $R_1$-$R_6$ are independently a hydrogen or an alkyl wherein $R_2$ and $R_3$ or $R_5$ and $R_6$ combine to form a 3-8 membered ring; $R_7$-$R_{16}$ are hydrogen, chloro, fluoro or a phosphoramidite; provided that at least two of $R_7$-$R_{16}$ are fluoro, and one of $R_7$-$R_{16}$ is L-O—P(O—CH$_2$CH$_2$CN)(N$R_{21}R_{22}$) wherein L is an alkyl linker, and $R_{21}$ and $R_{22}$ are isopropyl.

3.3. In another aspect of the invention, $R_1$ and $R_4$ are hydrogen; $R_2$ and $R_3$ combine to form cyclohexyl; $R_5$ and $R_6$ combine to form cyclohexyl; $R_7$-$R_{16}$ are hydrogen, chloro, fluoro or a phosphoramidite; provided that at least two of $R_7$-$R_{16}$ are fluoro, and one of $R_7$-$R_{16}$ is L-O—P(O—CH$_2$CH$_2$CN)(N$R_{21}R_{22}$) wherein L is an alkyl linker, and $R_{21}$ and $R_{22}$ are isopropyl.

3.4. In another aspect of the invention, $R_1$-$R_6$ are methyl; $R_7$-$R_{16}$ are hydrogen, chloro, fluoro or a phosphoramidite; provided that at least two of $R_7$-$R_{16}$ are fluoro, and one of $R_7$-$R_{16}$ is L-O—P(O—CH$_2$CH$_2$CN)(N$R_{21}R_{22}$) wherein L is an alkyl linker, and $R_{21}$ and $R_{22}$ are isopropyl.

3.5. In another aspect of the invention, $R_1$-$R_6$ are methyl; $R_9$ and $R_{12}$ are fluoro; $R_7$, $R_8$, $R_{10}$, $R_{11}$, $R_{13}$, $R_{14}$ and $R_{16}$ are hydrogen; $R_{15}$ is $C(=O)NH(CH_2)_n—O—P(O—CH_2CH_2CN)(NR_{21}R_{22})$ wherein n is 2-20, and $R_{21}$ and $R_{22}$ are isopropyl.

3.6. In another aspect of the invention, $R_1$-$R_6$ are methyl; $R_9$ and $R_{12}$ are fluoro; $R_7$, $R_8$, $R_{10}$, $R_{11}$, $R_{13}$, $R_{15}$ and $R_{16}$ are hydrogen; $R_{14}$ is $C(=O)NH(CH_2)_n—O—P(O—CH_2CH_2CN)(NR_{21}R_{22})$ wherein n is 2-20, and $R_{21}$ and $R_{22}$ are isopropyl.

3.7. In another aspect of the invention, $R_1$-$R_6$ are methyl; $R_9$ and $R_{12}$ are fluoro; $R_7$, $R_8$, $R_{10}$, $R_{11}$, $R_{13}$, $R_{14}$ and $R_{16}$ are hydrogen; $R_{15}$ is $C(=O)NH(CH_2CH_2O)_n—O—P(O—CH_2CH_2CN)(NR_{21}R_{22})$ wherein n is 2-20, and $R_{21}$ and $R_{22}$ are isopropyl.

3.8. In another aspect of the invention, $R_1$-$R_6$ are methyl; $R_9$ and $R_{12}$ are fluoro; $R_7$, $R_8$, $R_{10}$, $R_{11}$, $R_{13}$, $R_{15}$ and $R_{16}$ are hydrogen; $R_{14}$ is $C(=O)NH(CH_2CH_2O)_n-O-P(O-CH_2CH_2CN)(NR_{21}R_{22})$ wherein n is 2-20, and $R_{21}$ and $R_{22}$ are isopropyl.

The oligonucleotides prepared from compounds 3.1, 3.2, 3.3, 3.4, 3.5, 3.6, 3.7 and 3.8 typically exhibit a maximum fluorescence intensity at a pH between about 5.0 and about 8.0. Oftentimes, the oligonucleotides prepared from compounds of the invention exhibit a maximum fluorescence intensity at a pH between about 5.5 and about 8.0 or between about 6.0 and 8.0.

The oligonucleotides prepared from compounds 3.1, 3.2, 3.3, 3.4, 3.5, 3.6, 3.7 and 3.8 typically are substantially more resistant to photobleaching than the compound represented by Formula 2, where $R_{15}$ is $C(=O)NH(CH_2)_6-O-P(O-CH_2CH_2CN)(N-iPr_2)$.

Oftentimes the oligonucleotides prepared from the compounds of invention exhibit at least twice the percentage of initial fluorescence after 30 seconds when illuminated under the same conditions. In certain cases, the compounds exhibit at least three times, four times, five times, six times, seven times, eight times, nine times or ten times the percentage of initial fluorescence.

Oligonucleotides prepared from and/or including the compounds 3.1, 3.2, 3.3, 3.4, 3.5, 3.6, 3.7 and 3.8 typically exhibit a maximum fluorescence intensity at a pH between about 5.0 and about 8.0. Oftentimes, the oligonucleotides exhibit a maximum fluorescence intensity at a pH between about 5.5 and about 8.0 or between about 6.0 and 8.0.

Oligonucleotides prepared from and/or including the compounds 3.1, 3.2, 3.3, 3.4, 3.5, 3.6, 3.7 and 3.8 typically are substantially more resistant to photobleaching than oligonucleotides prepared from and/or including the compound of Formula 2. Oftentimes the oligonucleotides exhibit at least twice the percentage of initial fluorescence after 30 seconds when illuminated under the same conditions. In certain cases, the oligonucleotides exhibit at least three times, four times, five times, six times, seven times, eight times, nine times or ten times the percentage of initial fluorescence.

Synthesis

The compounds of the invention may be prepared using any suitable synthetic schemes. The methodology used to prepare the compounds of the invention may involve two components. The first component may involve the formation of the dye, while the second may involve the modification of the dye by forming a phosphoramidite group. Although these synthetic components are typically performed in the order given, they may be carried out in any other suitable sequences. For example, a portion of the dye may be derivatized with a protection group prior to formation of the phosphoramidite group. The appropriate methods may be used to synthesize the desired compounds of the invention.

The syntheses of fluorescein dyes have been well described in Examples 1-9. Analogous syntheses are also described in the literature (U.S. Pat. No. 4,439,356; U.S. Pat. No. 5,066,580; U.S. Pat. No. 5,583,236; U.S. Pat. No. 5,637,733; U.S. Pat. No. 6,162,931; U.S. Pat. No. 6,221,604; U.S. Pat. No. 8,084,627; WO 2013/122189; WO 2017/201531). These methods can be readily adapted to prepare dye intermediates useful for the synthesis of the compounds of the invention.

Synthesis of conventional xanthene dyes such as fluoresceins, rhodamines and rhodols typically involves the condensation of two equivalents of resorcinol (for fluoresceins), aminophenol (for rhodamines) or a mixture of a resorcinol and an aminophenol (for rhodols) with a carbonyl-containing moiety such as a phthalic acid derivative or benzaldehyde derivatives. However, in the synthesis of the xanthene indicators of the invention, the desired resorcinol or aminophenol is condensed with a carboxylic acid, anhydride or acyl halide.

Alternatively, the fluorescent xanthene of the invention can be prepared via the condensation of properly protected xanthones. This organometallic chemistry is well described in the literature (U.S. Pat. No. 5,049,673; U.S. Pat. No. 5,453,517; U.S. Pat. No. 5,501,980; U.S. Pat. No. 5,459,276; U.S. Pat. No. 5,501,980; U.S. Pat. No. 5,459,276; and U.S. Pat. No. 5,516,911; U.S. Pat. No. 8,779,165; U.S. Pat. No. 8,927,224; U.S. Pat. No. 9,097,730; U.S. Pat. No. 9,279,817; C. Chen, R. Yeh and D. S. Lawrence, J. Am. Chem. Soc. 2002, 124, 3840; U.S. Pat. No. 5,049,673); Y. Urano, M. Kamiya, K. Kanda, T. Ueno, K. Hirose and T. Nagano, J. Am. Chem. Soc. 2005, 127, 4888) and can be readily adapted to synthesize the compounds of the invention (X. Zhou et al., Angew. Chem. Int. Ed., 2017, 56, 4197; M. Sednev et al., Bioconjugate Chem., 2013, 24, 690; K. Kolmakov et. al., Eur. J Chem. 2010, 3593; Y. Koide et. al., ACS Chem. Biol., 2011, 6, 600).

Post-condensation modifications of the fluorophore moieties are typically analogous to known methods. For example, the reduction of nitro substituents to amino groups, the conversion of carboxy substituents to cyano groups, and the preparation of esters and amides of carboxylic acids. Additionally, a given salt or counterion of the indicators of the invention may be readily converted to other salts by treatment with ion-exchange resins, selective precipitation, and basification, as is well-known in the art. Post-condensation modifications of xanthylium dyes are well known. For instance, the xanthenone portion of the dye can be halogenated by treatment with an appropriate halogenating agent, such as liquid bromine. Xanthenes containing unsaturated fused rings can be hydrogenated to the saturated derivatives.

The reduced and oxidized versions of the xanthene indicators are freely interconvertible by well-known oxidation or reduction reagents, including borohydrides, aluminum hydrides, hydrogen/catalyst, and dithionites. A variety of oxidizing agents mediate the oxidation of dihydroxanthenes, including molecular oxygen in the presence or absence of a catalyst, nitric oxide, peroxynitrite, dichromate, triphenylcarbenium and chloranil. The dihydroxanthenes may also be oxidized electrochemically, or by enzyme action, including the use of horseradish peroxidase in combination with peroxides or by nitric oxide.

The preparations of phosphoramidite compounds have been well described in Examples 7 and 10. Analogous syntheses are also described in the literature (U.S. Pat. No. 5,231,191; U.S. Pat. No. 5,212,304; U.S. Pat. No. 5,556,959; U.S. Pat. No. 5,583,236; U.S. Pat. No. 5,808,044; U.S. Pat. No. 6,331,632; U.S. Pat. No. 7,030,230; U.S. Pat. No. 7,230,117; U.S. Pat. No. 8,084,589). These methods can be readily adapted to prepare the compounds of the invention.

The preparations of fluorescent oligonucleotides have been well automated by the utilization of various commercial oligonucleotide synthesizers with dye phosphoramidites (M. J. Gait, Oligonucleotide Synthesis, a Practical Approach, 1984). There are now a large number of commercial vendors that offer overnight delivery of fluorescent oligonucleotides as long as dye phosphoramidites are available, and the desired oligonucleotide sequences are given. These vendors include Integrated DNA Technologies, Sigma-Aldrich, ThermoFisher, Eurofins, Biosynthesis, Bioneer, Genscript, Trilink Biotech and Biosearch etc.

Applications of the Fluorescent Indicators of the Invention

The examples provided below illustrate selected aspects of the invention. They are not intended to limit or define the entire scope of the invention.

EXAMPLES

Example 1. Preparation of Compound 2

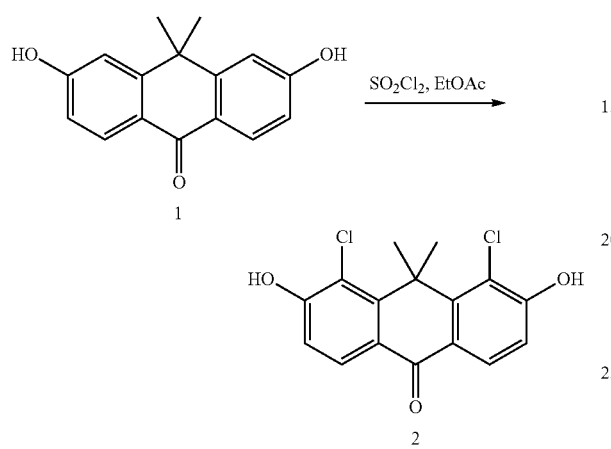

Compound 1 is prepared as described by J. B. Grimm et al (ACS Chemical Biology, 2013, 8, 1303). Compound 1 (3.33 g) is dissolved in EtOAc (100 mL). To the solution of Compound 1, $SO_2Cl_2$ (2.3 mL) is added. The reaction mixture is stirred at room temperature. Additional $SO_2Cl_2$ (2×0.6 mL) is added in 2 batches within 2 hours. The reaction is quenched with ice-water after 4 hours. The organic layer is collected, dried with sodium sulfate, filtered and concentrated. The residue is purified by flash chromatography (hexane-EtOAc, 0-80%) to give compound 2 as a yellow solid (3.86 g).

Example 2. Preparation of Compound 3

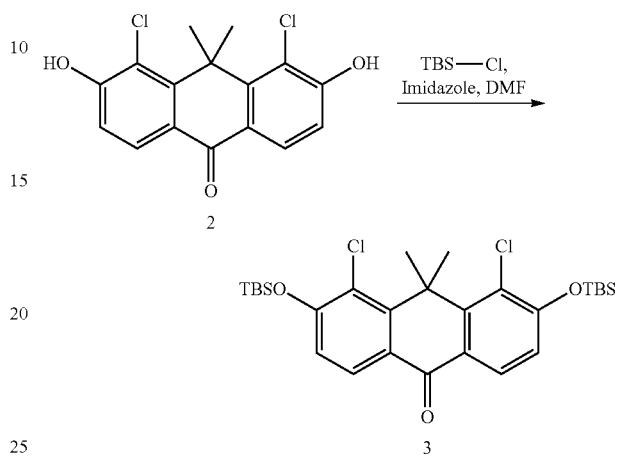

Compound 2 (2.96 g) and imidazole (3.75 g) are dissolved in DMF (45 mL). To the DMF solution TBS-Cl (4.16 g) is added. The reaction is stirred at room temperature for 20 hours before being diluted with EtOAc. The mixture is washed with water and brine, dried with sodium sulfate, filtered and concentrated. The residue is purified by flash chromatography (hexane-EtOAc, 0-10%) to give compound 3 as a white solid (3.03 g).

Example 3. Preparation of Compound 5

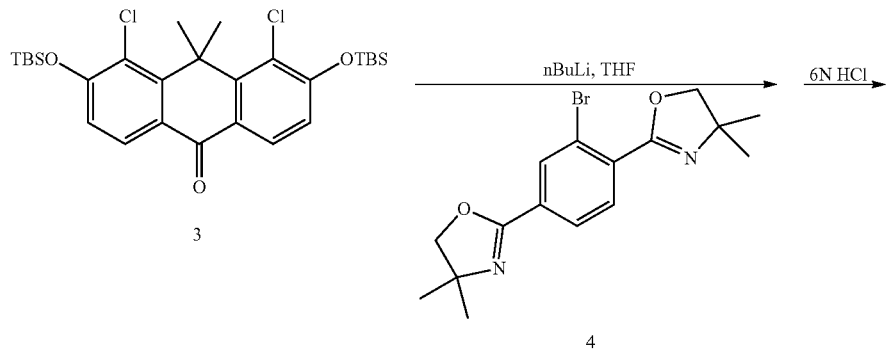

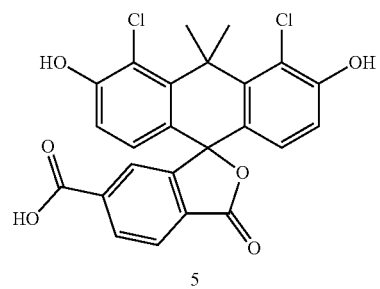

Compound 4 is prepared as described by G. Lukinavicius et al (Nature Chemistry, 2013, 5, 132). Compound 4 (2.10 g) is dissolved in THF (23 mL) and cooled to −78° C. To the solution nBuLi (2.40 mL, 2.5 M in hexane) is added slowly and stirred for 40 minutes at −78° C. The solution of compound 3 (2.80 g) in THF (20 mL) is added. The reaction mixture is warmed to 0° C. After 30 minutes, the reaction is quenched with excess saturated ammonium chloride solution and extracted with EtOAc. The organic layer is collected, dried with sodium sulfate, filtered and concentrated. The residue is dissolved in dioxane (50 mL), and to the dioxane solution 6N HCl (90 mL) is added. The mixture is stirred at 95° C. for 6 hours before being diluted with water and extracted with EtOAc. The organic layer is collected, dried with sodium sulfate, filtered and concentrated. The residue is purified by flash chromatography (a gradient of 0-75% DCM-EtOAc with 1% AcOH) to give compound 5 as an orange solid (3.00 g).

Example 4. Preparation of Compound 7

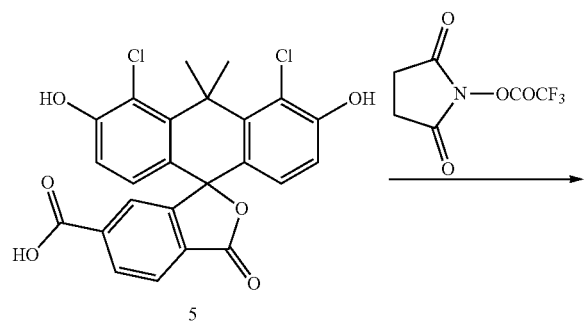

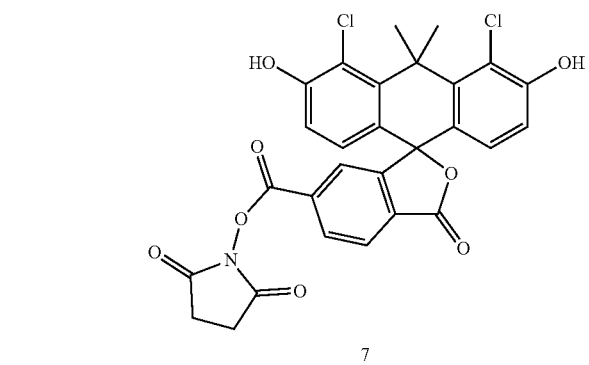

Compound 5 (2.06 g) is dissolved in a mixture of THF (24 mL) and pyridine (8 mL). To the THF solution added is N-succinimidyl trifluoroacetate (2.03 g), and the reaction mixture is stirred at room temperature for 30 mins. The mixture is concentrated, diluted with EtOAc, washed by 1N HCl-ice. The organic layer is collected, dried with sodium sulfate, filtered and concentrated to give compound 7 as an orange solid (2.10 g).

Example 5. Preparation of Compound 9

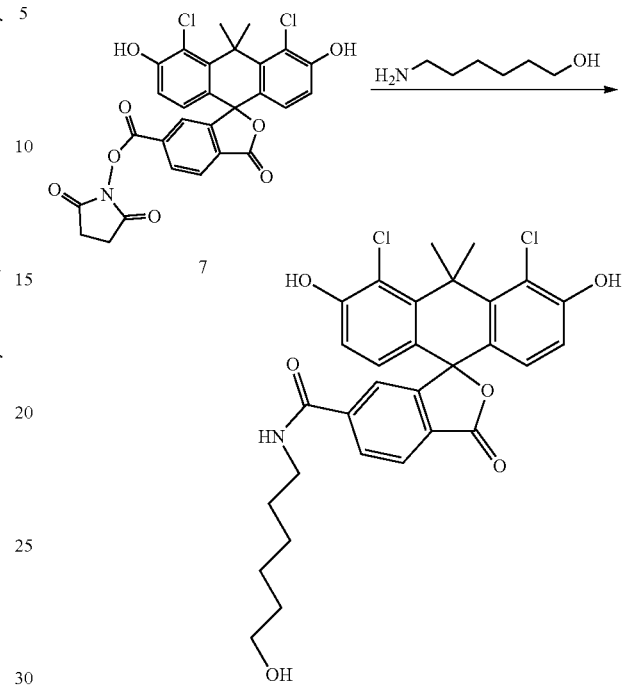

6-Amino-1-hexanol (1.13 g) is dissolved in THF (20 mL), and to the THF solution added is Et₃N (2.60 mL). To the reaction mixture are added Compound 7 (2.10 g) in THF (25 mL)-DMF (15 mL). The reaction mixture is stirred at room temperature for 2 hours, concentrated under high vacuum, diluted with EtOAc and acidified with 0.5N HCl-ice. The organic layer is collected, dried with sodium sulfate, filtered and concentrated. The residue is purified by flash chromatography (DCM-MeOH, 0-20%) to give compound 9 as a yellow solid (3.00 g).

Example 6. Preparation of Compound 11

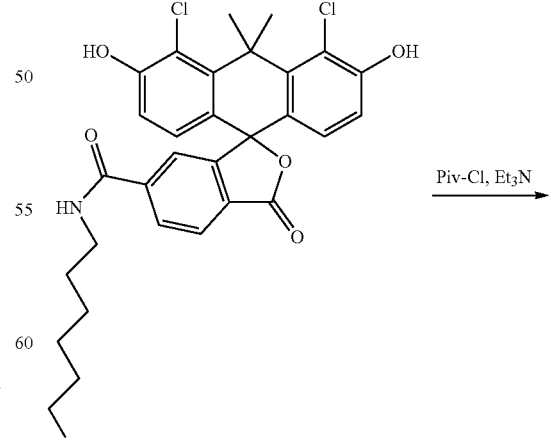

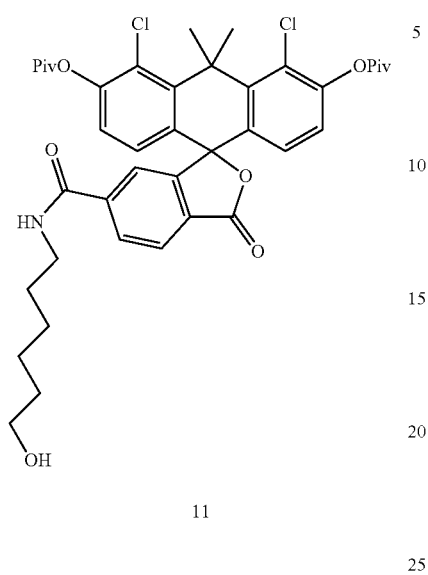

11

Compound 9 (2.40 g) is suspended in DCM (50 mL), to the DCM suspension added is Et₃N (1.30 mL). To the red suspension added is pivaloyl chloride (1.15 mL) in ice bath. The reaction is continued in ice bath for 2 hours before being quenched with 0.6N HCl. The mixture is extracted by DCM, and the organic layer is collected, dried with sodium sulfate, filtered and concentrated. The residue is purified by flash chromatography (DCM-EtOAc, 0-70%) to give compound 11 as a yellow solid (1.66 g).

Example 7. Preparation of Compound 13

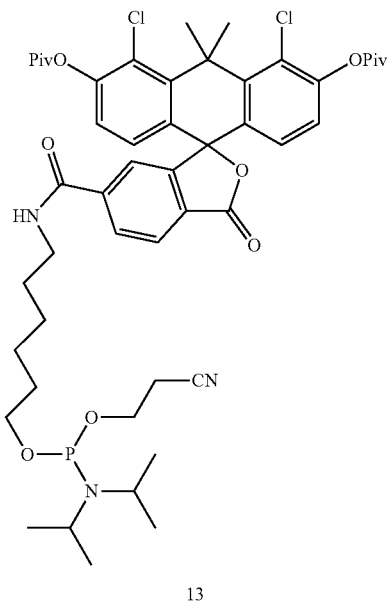

13

Compound 11 (1.41 g) is dissolved in DCM (10 mL), and to the DCM solution added are tetrazole diisopropylamine (0.324 g) and 2-cyanoethyl N,N,N',N'-tetraisopropylphosphorodiamidite (0.72 mL). The reaction mixture is stirred at room temperature for 1 hour and diluted with DCM. The mixture is washed with saturated sodium bicarbonate solution and brine. The organic layer is collected, dried with sodium sulfate, filtered and concentrated. The residue is purified by flash chromatography (a gradient of 20-70% hexane-EtOAc with 1% Et₃N) to give compound 13 as a white solid (0.96 g).

Example 8. Preparation of Compound 16

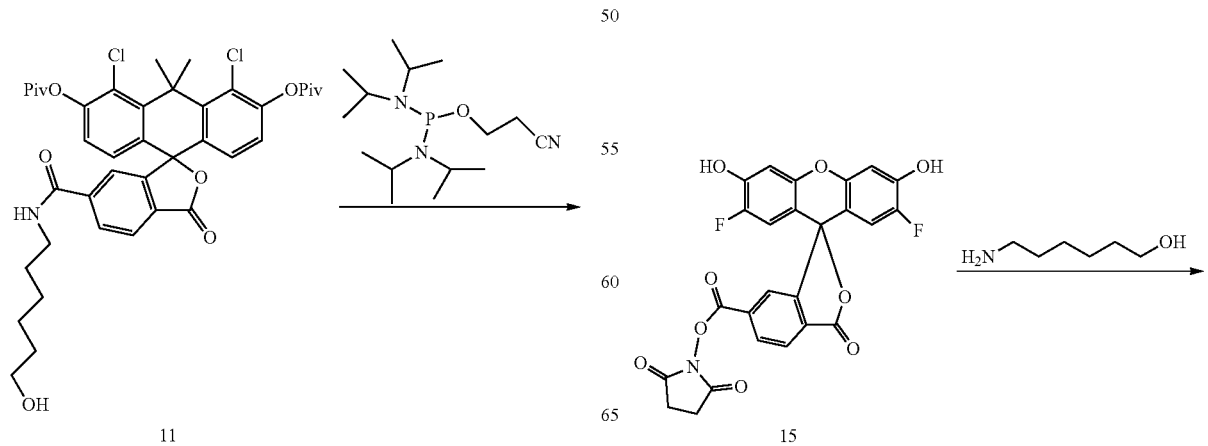

11  15

17

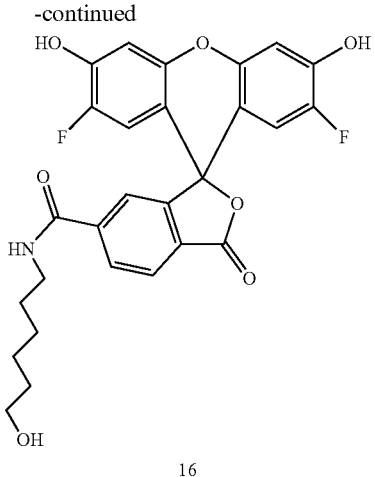

16

6-Amino-1-hexanol (10 g) and Et₃N (20 mL) are dissolved in DMF (50 mL). To the reaction mixture are added Compound 15 (10 g, AAT Bioquest) in DMF (100 mL). The reaction mixture is stirred at room temperature for 2 hours, concentrated under high vacuum, diluted with EtOAc and acidified with 0.5N HCl-ice. The mixture is filtered to collect the solid that is dried under high vacuum. The crude solid is purified by flash chromatography (DCM-MeOH, 0-20%) to give compound 16 as a yellow solid (11 g).

Example 9. Preparation of Compound 18

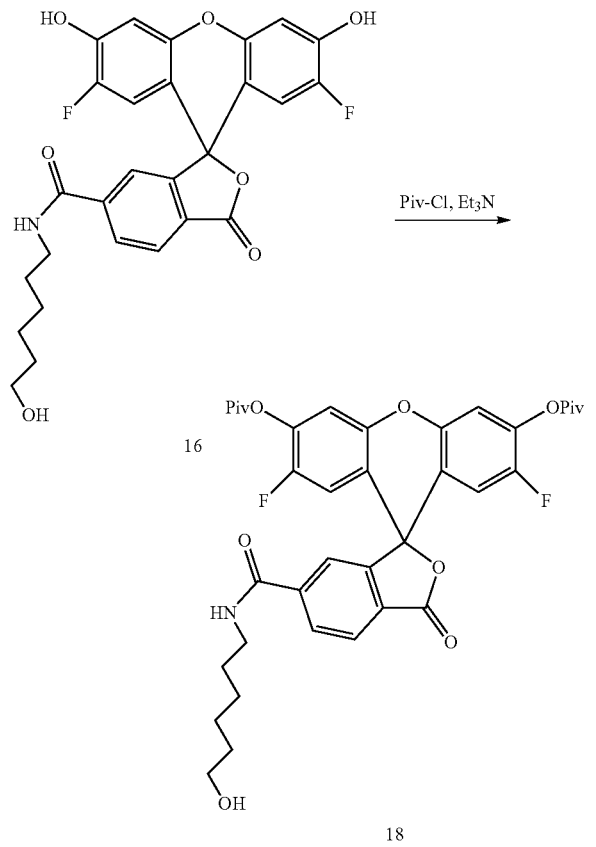

18

Compound 16 (10 g) is suspended in DCM (200 mL), to the DCM suspension added is Et₃N (10 mL). To the red suspension added is pivaloyl chloride (10 mL) in ice bath. The reaction is continued in ice bath for 2 hours before being quenched with 0.6N HCl. The mixture is extracted by DCM, and the organic layer is collected, dried with sodium sulfate, filtered and concentrated. The residue is purified by flash chromatography (DCM-EtOAc, 0-70%) to give compound 18 as a yellow solid (12 g).

Example 10. Preparation of Compound 20

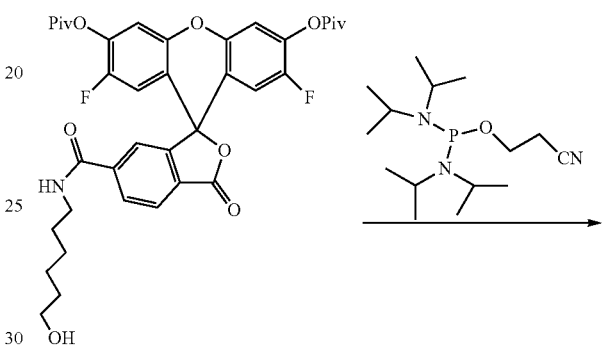

18

20

Compound 18 (10 g) is dissolved in DCM (10 mL), and to the DCM solution added are tetrazole diisopropylamine (1.5 g) and 2-cyanoethyl N,N,N',N'-tetraisopropylphosphorodiamidite (4 mL). The reaction mixture is stirred at room temperature for 2 hours and diluted with DCM. The mixture is washed with saturated sodium bicarbonate solution and brine. The organic layer is collected, dried with sodium sulfate, filtered and concentrated. The residue is purified by flash chromatography (a gradient of 20-70% hexane-EtOAc with 1% Et₃N) to give compound 20 as a white solid (12 g).

Example 11. Preparation of Compound 30
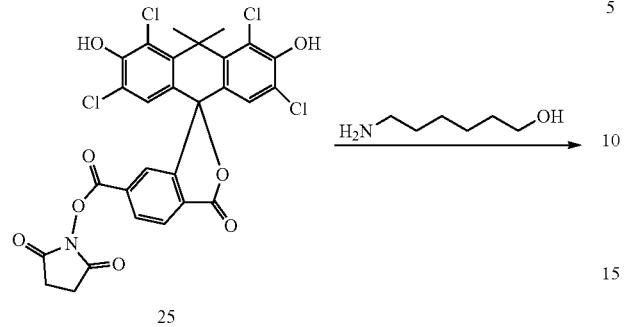
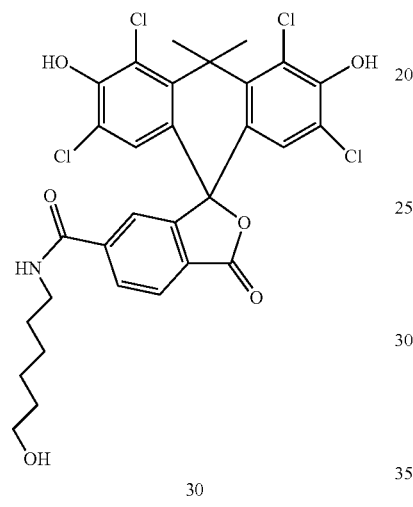
30
Compound 30 is prepared analogously to the procedure of Compound 16 by reacting Compound 25 (AAT Bioquest) with 6-Amino-1-hexanol.
Example 12. Preparation of Compound 31
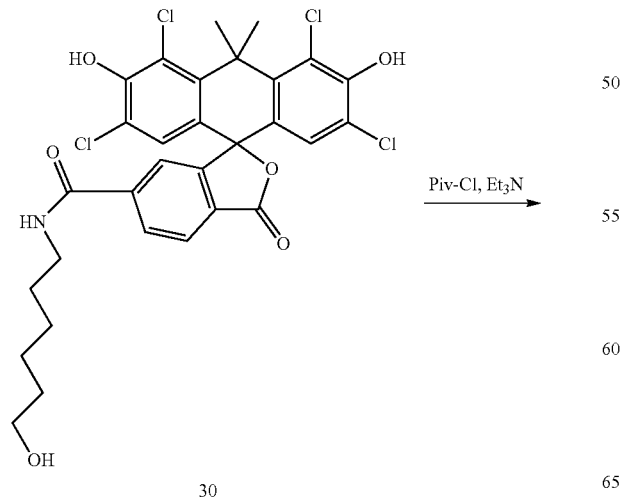
30
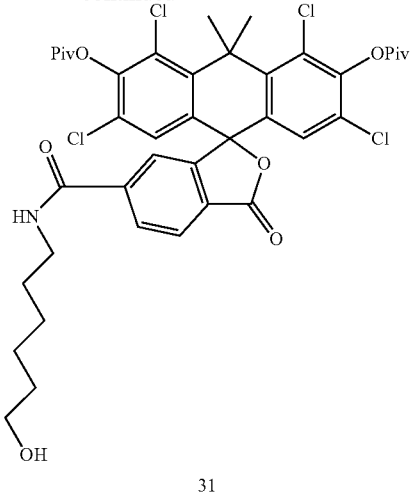
31
Compound 30 is converted to Compound 31 analogously to the procedure of Compound 18 by reacting Compound 30 with pivaloyl chloride.
Example 13. Preparation of Compound 35
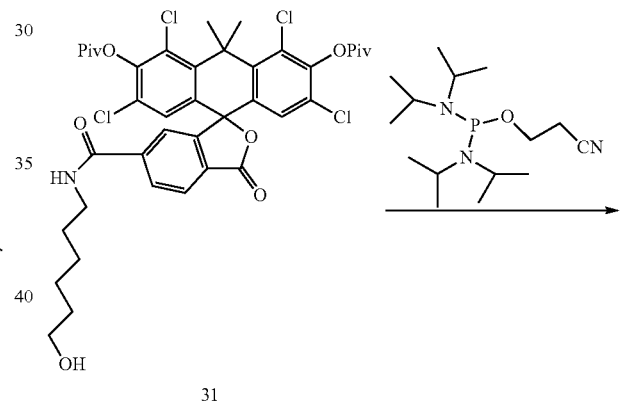
31
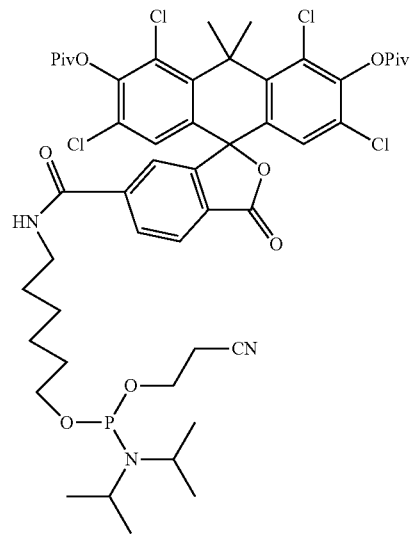
35

Compound 31 is converted to Compound 35 analogously to the procedure of Compound 20 by reacting Compound 31 with 2-cyanoethyl N,N,N',N'-tetraisopropylphosphorodiamidite.

Example 14. Preparation of Compound 40

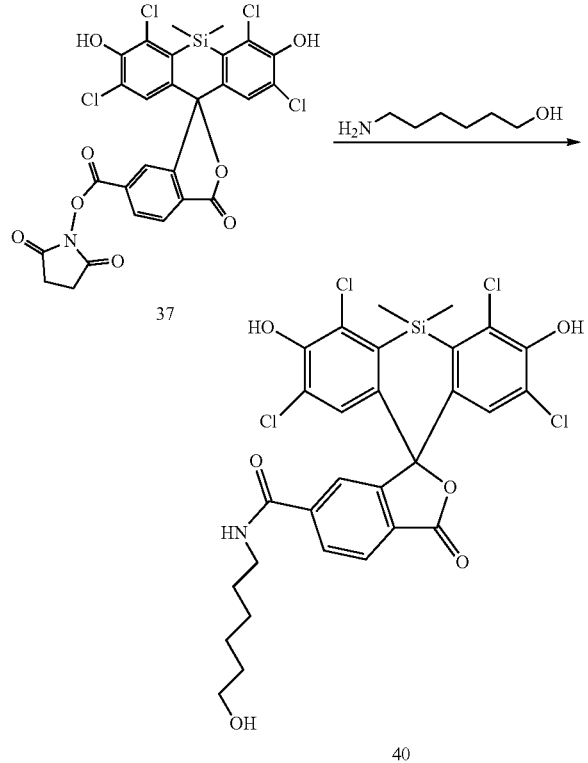

Compound 30 is prepared analogously to the procedure of Compound 16 by reacting Compound 37 (AAT Bioquest) with 6-Amino-1-hexanol.

Example 15. Preparation of Compound 44

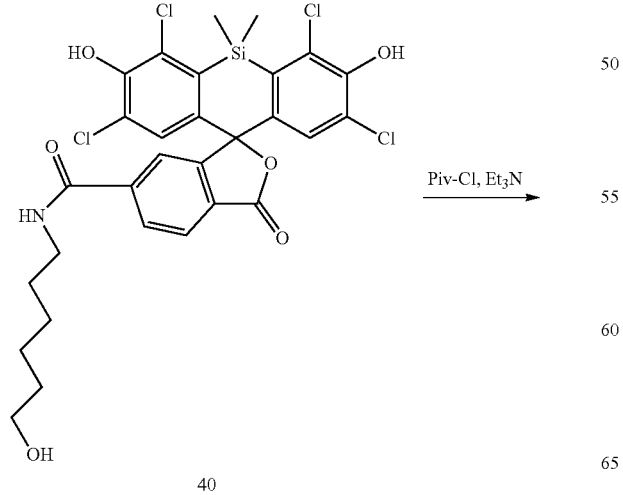

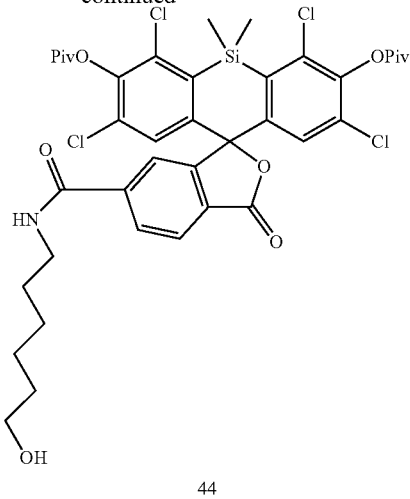

Compound 40 is converted to Compound 44 analogously to the procedure of Compound 18 by reacting Compound 40 with pivaloyl chloride.

Example 16. Preparation of Compound 48

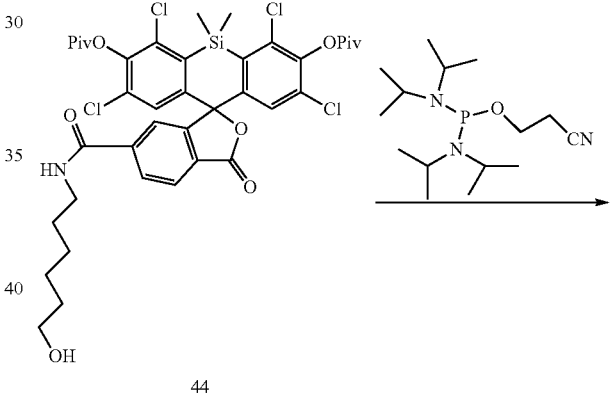

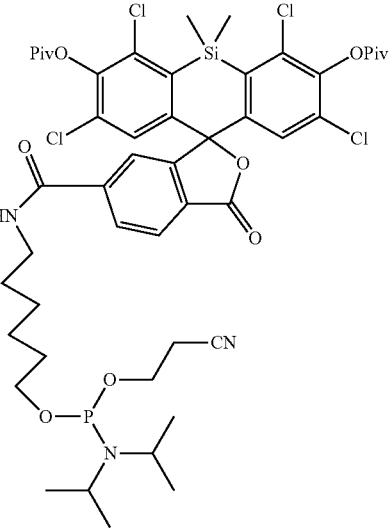

Compound 44 is converted to Compound 48 analogously to the procedure of Compound 20 by reacting Compound 44 with 2-cyanoethyl tetraisopropylphosphorodiamidite.

Example 17. Preparation of Compound 50

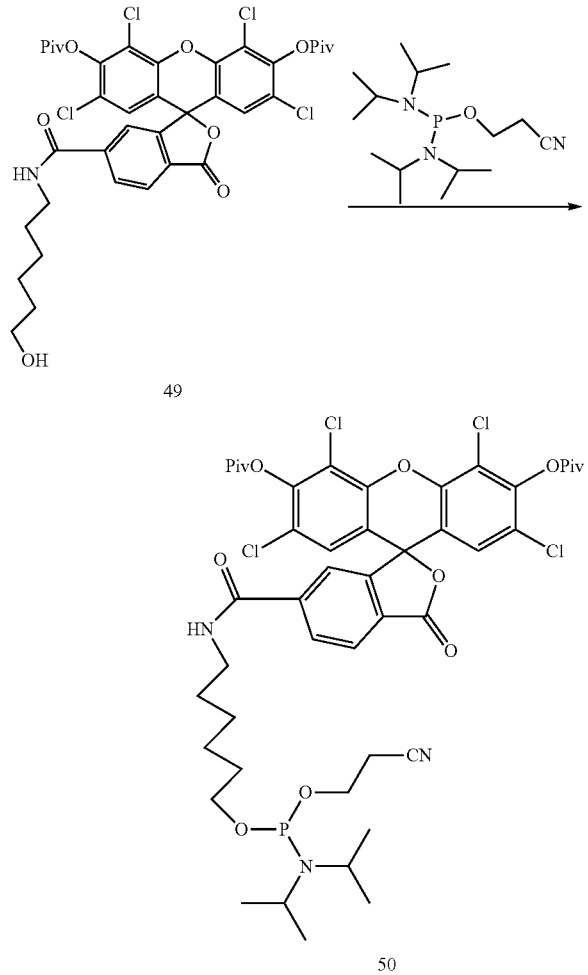

Compound 49 (Xian Biolite) is converted to Compound 50 analogously to the procedure of Compound 20 by reacting Compound 49 with 2-cyanoethyl N,N,N',N'-tetraisopropylphosphorodiamidite.

Example 18. Use of the Oligonucleotides Prepared from the New Fluorescein Phosphoramidites for Molecular Biological Detections

[Compound 9]-CGACGGAGTCCTTCCACGATAC-CACGTCG-TQ3 (SEQ ID NO: 1) is synthesized, and used as a GAPDH-targeting molecular beacon that uses TQ3 as a quencher and Compound 9 as a fluorophore. The molecular beacon is mixed with the samples containing the complementary sequence fragment "TGGTATCGTG-GAAGGACTC" (SEQ ID NO: 2). The fluorescence intensities are monitored with the samples (under a gradient concentrations) by a fluorescence microplate reader. The fluorescence signals of molecular beacon in the absence of target is recorded as the background signal. The random molecular beacons (do not have any match in the entire human genome) are incubated with target sequence as a negative control to verify the hybridization specificity. All the assays are performed in PBS buffer.

HeLa cells are cultured in eight well chambered cover slides for 24 h in normal growth medium, and washed with PBS buffer (without calcium or magnesium). The slide is fixed in 100% methanol at −20° C. for 10 min. After removing methanol, the slides are allowed to be air-dried and stored overnight at −80° C. In situ hybridization assays are performed by first washing the slides for 5 min in PBS and hybridizing them overnight at 37° C. in PBS (without calcium or magnesium) containing 200 nM of the above GAPDH-targeting molecular beacon ([Compound 9]-CGACGGAGTCCTTCCACGATACCACGTCG-TQ3 (SEQ ID NO: 1)). The cells are also incubated with random beacons under the same conditions as a negative control. After removing the hybridization solution with washing and adding PBS, the cells are imaged with a fluorescence microscope.

Although the present invention has been shown and described with reference to the foregoing operational principles and preferred embodiments, it will be apparent to those skilled in the art that various changes in form and detail may be made without departing from the spirit and scope of the invention. The present invention is intended to embrace all such alternatives, modifications and variances that fall within the scope of the appended claims.

What is claimed is:

1. A phosphoramidite having Formula 1:

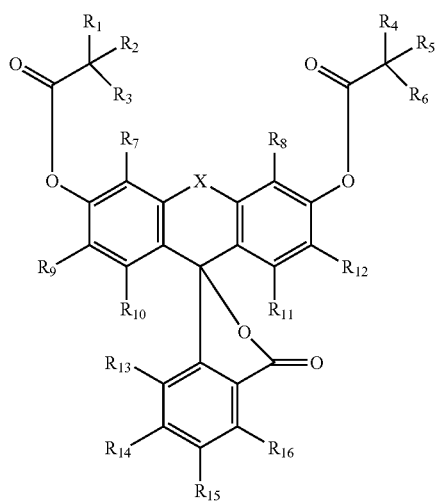

Formula 1 wherein $R_1$-$R_6$ are independently a hydrogen, an alkyl, an aryl or a heteroaryl; $R_7$-$R_{16}$ are independently H, an alkyl, a halogen, carboxy, an alkoxy, an aryloxy, thiol, a alkylthiol, an arylthiol, azido, nitro, nitroso, cyano, an amino, hydroxy, a phosphonyl, a sulfonyl, a carbonyl, a boronyl, an aryl, a heteroaryl or a phosphoramidite; X is N—$R_{18}$, P—$R_{18}$, O=P—$R_{18}$, O=P—$OR_{18}$, $R_{18}$—C—$R_{19}$, $R_{18}$—Si—$R_{19}$, S, O=S—$R_{18}$ or O=S(O)—$R_{18}$; provided that one of $R_7$-$R_{19}$ is L-O—P(O—$R_{20}$)($NR_{21}R_{22}$) wherein L is none or a linker, $R_{18}$ to $R_{22}$ are an alkyl, an aryl or a heteroaryl.

2. The compound of claim 1, $R_1$-$R_6$ are independently a hydrogen or an alkyl; $R_7$-$R_{16}$ are independently H, an alkyl, a halogen, an aryl, a heteroaryl or a phosphoramidite; X is O=P—$R_{18}$, O=P—$OR_{18}$, $R_{18}$—C—$R_{19}$, or $R_{18}$—Si—$R_{19}$; provided that one of $R_7$-$R_{19}$ is L-O—P(O—$R_{20}$)($NR_{21}R_{22}$) wherein L is none or a linker, $R_{18}$ to $R_{22}$ are an alkyl, an aryl or a heteroaryl.

3. The compound of claim 1, $R_1$-$R_6$ are methyl; $R_7$-$R_{16}$ are independently H, chloro, fluoro, an aryl, a heteroaryl, or phosphoramidite; X is $R_{18}$—C—$R_{19}$ or $R_{18}$—Si—$R_{19}$; provided that one of $R_7$-$R_{19}$ is L-O—P(O—$CH_2CH_2CN$)($NR_{21}R_{22}$) wherein L is an alkyl linker, and $R_{21}$ and $R_{22}$ are isopropyl.

4. The compound of claim 3, L is C(=O)NH($CH_2)_n$—O—P(O—$CH_2CH_2CN$)($NR_{21}R_{22}$) wherein n is 2-20.

5. The compound of claim 3, L is C(=O)NH($CH_2$ $CH_2O)_n$—O—P(O—$CH_2CH_2CN$)($NR_{21}R_{22}$) wherein n is 1-20.

6. The compound of claim 3, $R_{18}$ and $R_{19}$ are methyl.

7. The compound of claim 1, $R_1$-$R_6$ are methyl; $R_7$-$R_{16}$ are independently H, chloro, fluoro, an aryl, a heteroaryl, or phosphoramidite; X is $R_{18}$—C—$R_{19}$ or $R_{18}$—Si—$R_{19}$ wherein $R_{18}$ and $R_{19}$ combine to form a 3-8 member ring structure; provided that one of $R_7$-$R_{19}$ is L-O—P(O—$CH_2CH_2CN$)($NR_{21}R_{22}$) wherein L is an alkyl linker, and $R_{21}$ and $R_{22}$ are isopropyl.

8. The compound of claim 5, $R_{18}$ and $R_{19}$ combine to form cyclohexyl.

9. The compound of claim 1, $R_1$-$R_6$ are independently a hydrogen or an alkyl wherein $R_2$ and $R_3$ or $R_5$ and $R_6$ combine to form a 3-8 membered ring structure; $R_7$-$R_{16}$ are hydrogen, chloro, fluoro or a phosphoramidite; X is $R_{18}$—C—$R_{19}$ or $R_{18}$—Si—$R_{19}$; provided that one of $R_7$-$R_{19}$ is L-O—P(O—$CH_2CH_2CN$)($NR_{21}R_{22}$) wherein L is an alkyl linker, and $R_{21}$ and $R_{22}$ are isopropyl.

10. The compound of claim 1, $R_2$ and $R_3$ combine to form cyclohexyl; $R_5$ and $R_6$ combine to form cyclohexyl.

11. A phosphoramidite having Formula 3:

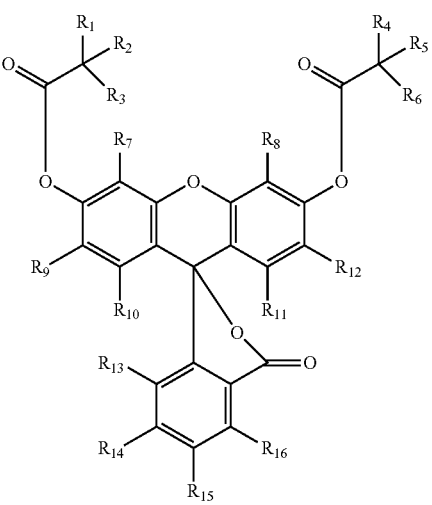

Formula 3 wherein $R_1$-$R_6$ are independently a hydrogen or an alkyl; $R_7$-$R_{16}$ are hydrogen, chloro, fluoro or a phosphoramidite; provided that at least two of $R_7$-$R_{16}$ are fluoro, and one of $R_7$-$R_{16}$ is L-O—P(O—$R_{20}$)($NR_{21}R_{22}$) wherein L is none or a linker, and $R_{20}$ to $R_{22}$ are an alkyl or an aryl.

12. The compound of claim 11, $R_1$-$R_6$ are methyl; $R_9$ and $R_{12}$ are fluoro; $R_7$, $R_8$, $R_{10}$, $R_{11}$, $R_{13}$, $R_{15}$ and $R_{16}$ are hydrogen; $R_{14}$ is C(=O)NH($CH_2)_n$—O—P(O—$CH_2CH_2CN$)($NR_{21}R_{22}$) wherein n is 2-20, and $R_{21}$ and $R_{22}$ are isopropyl.

13. The compound of claim 11, $R_1$-$R_6$ are methyl; $R_9$ and $R_{12}$ are fluoro; $R_7$, $R_8$, $R_{10}$, $R_{11}$, $R_{13}$, $R_{14}$ and $R_{16}$ are hydrogen; $R_{15}$ is C(=O)NH($CH_2CH_2O)_n$—O—P(O—$CH_2CH_2CN$)($NR_{21}R_{22}$) wherein n is 2-20, and $R_{21}$ and $R_{22}$ are isopropyl.

14. The compound of claim 11, $R_1$-$R_6$ are independently a hydrogen or an alkyl wherein $R_2$ and $R_3$ or $R_5$ and $R_6$ combine to form a 3-8 membered ring; $R_7$-$R_{16}$ are hydrogen, chloro, fluoro or a phosphoramidite; provided that at least two of $R_7$-$R_{16}$ are fluoro, and one of $R_7$-$R_{16}$ is L-O—P(O—CH$_2$CH$_2$CN)(NR$_{21}$R$_{22}$) wherein L is an alkyl linker, and $R_{21}$ and $R_{22}$ are isopropyl.

15. The compound of claim 11, $R_1$ and $R_4$ are hydrogen; $R_2$ and $R_3$ combine to form cyclohexyl; $R_5$ and $R_6$ combine to form cyclohexyl.

16. A fluorescent oligonucleotide prepared from the phosphoramidite having Formula 1:

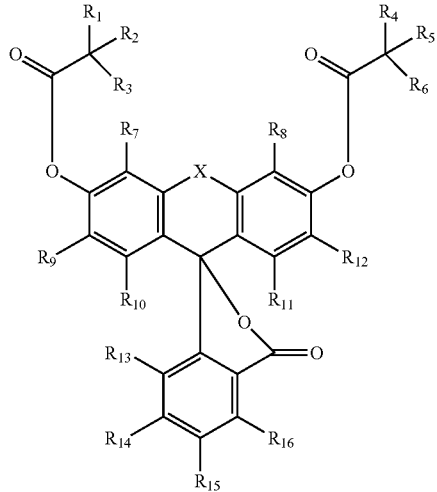

Formula 1 wherein $R_1$-$R_6$ are independently a hydrogen, an alkyl, an aryl or a heteroaryl; $R_7$-$R_{16}$ are independently H, an alkyl, a halogen, an aryl, a heteroaryl or a phosphoramidite; X is O=P—$R_{18}$, O=P—OR$_{18}$, $R_{18}$—C—$R_{19}$ or $R_{18}$—Si—$R_{19}$; provided that one of $R_7$-$R_{19}$ is L-O—P(O—$R_{20}$)(NR$_{21}$R$_{22}$) wherein L is none or a linker, $R_{18}$ to $R_{22}$ are an alkyl, an aryl or a heteroaryl.

17. A fluorescent oligonucleotide of claim 16, $R_1$-$R_6$ are methyl; $R_7$-$R_{16}$ are independently H, chloro, fluoro, an aryl, a heteroaryl or a phosphoramidite; X is CH$_3$—C—CH$_3$ or CH$_3$—Si—CH$_3$; provided that one of $R_7$-$R_{19}$ is L-O—P(O—CH$_2$CH$_2$CN)(NR$_{21}$R$_{22}$) wherein L is an alkyl linker, and $R_{21}$ and $R_{22}$ are isopropyl.

18. A fluorescent oligonucleotide prepared from the phosphoramidite having Formula 3:

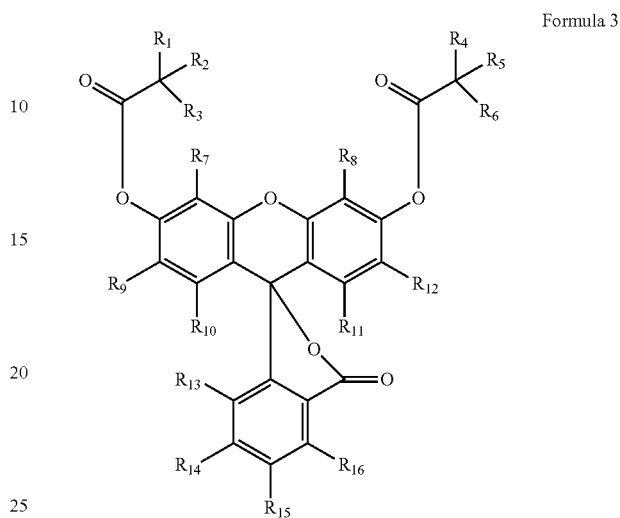

Formula 3 wherein $R_1$-$R_6$ are methyl; $R_7$-$R_{16}$ are hydrogen, chloro, fluoro or a phosphoramidite; provided that at least two of $R_7$-$R_{16}$ are fluoro, and one of $R_{14}$ and $R_{15}$ is L-O—P(O—CH$_2$CH$_2$CN)(NR$_{21}$R$_{22}$) wherein $R_{21}$ and $R_{22}$ are isopropyl.

19. A fluorescent oligonucleotide of claim 18, $R_9$ and $R_{12}$ are fluoro; $R_7$, $R_8$, $R_{10}$, $R_{11}$, $R_{13}$, $R_{15}$ and $R_{16}$ are hydrogen; $R_{14}$ is C(=O)NH(CH$_2$)$_n$—O—P(O—CH$_2$CH$_2$CN)(NR$_{21}$R$_{22}$) or wherein n is 2-20, and $R_{21}$ and $R_{22}$ are isopropyl.

20. A fluorescent oligonucleotide of claim 18, $R_9$ and $R_{12}$ are fluoro; $R_7$, $R_8$, $R_{10}$, $R_{11}$, $R_{13}$, $R_{14}$ and $R_{16}$ are hydrogen; $R_{15}$ is C(=O)NH(CH$_2$)$_n$—O—P(O—CH$_2$CH$_2$CN)(NR$_{21}$R$_{22}$) wherein n is 2-20, and $R_{21}$ and $R_{22}$ are isopropyl.

* * * * *

SEQUENCE LISTING

<160> NUMBER OF SEQ ID NOS: 2

<210> SEQ ID NO 1
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 1
cgacggagtc cttccacgat accacgtcg                29

<210> SEQ ID NO 2
<211> LENGTH: 19
<212> TYPE: DNA
<213> ORGANISM: Artificial Sequence

```
<220> FEATURE:
<223> OTHER INFORMATION: Synthetic oligonucleotide

<400> SEQUENCE: 2
tggtatcgtg gaaggactc                                              19
```